US008728499B2

(12) United States Patent
Zawko et al.

(10) Patent No.: US 8,728,499 B2
(45) Date of Patent: May 20, 2014

(54) DENDRITIC MACROPOROUS HYDROGELS PREPARED BY CRYSTAL TEMPLATING

(71) Applicants: Scott Zawko, Austin, TX (US); Christine Schmidt, Gainesville, FL (US)

(72) Inventors: Scott Zawko, Austin, TX (US); Christine Schmidt, Gainesville, FL (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/909,707

(22) Filed: Jun. 4, 2013

(65) Prior Publication Data

US 2013/0266618 A1    Oct. 10, 2013

Related U.S. Application Data

(63) Continuation of application No. 12/919,667, filed as application No. PCT/US2009/035257 on Feb. 26, 2009.

(60) Provisional application No. 61/031,651, filed on Feb. 26, 2008.

(51) Int. Cl.
| | | |
|---|---|---|
| A61K 9/00 | (2006.01) | |
| A61K 9/70 | (2006.01) | |
| A61K 9/14 | (2006.01) | |
| A61F 13/00 | (2006.01) | |

(52) U.S. Cl.
USPC ............................. 424/400; 424/443; 424/488

(58) Field of Classification Search
CPC ................ A61K 31/734; A61K 47/36; A61K 47/48784; A61K 9/0024; A61K 31/728
USPC .......................................... 424/400, 443, 488
See application file for complete search history.

(56) References Cited

U.S. PATENT DOCUMENTS

| | | |
|---|---|---|
| 4,141,973 A | 2/1979 | Balazs |
| 4,196,070 A | 4/1980 | Chao |
| 4,818,542 A | 4/1989 | DeLuca |
| 4,937,270 A | 6/1990 | Hamilton |
| 5,017,229 A | 5/1991 | Burns |
| 5,531,716 A | 7/1996 | Luzio |
| 5,531,735 A | 7/1996 | Thompson |
| 5,563,186 A | 10/1996 | Thompson |
| 5,622,707 A | 4/1997 | Dorigatti |
| 5,714,166 A | 2/1998 | Tomalia |
| 5,750,585 A | 5/1998 | Park |
| 5,760,200 A | 6/1998 | Miller |
| 5,863,551 A | 1/1999 | Woerly |
| 5,919,442 A | 7/1999 | Yin |
| 5,939,323 A | 8/1999 | Valentini |
| 5,993,661 A | 11/1999 | Ruckenstein |
| 6,007,833 A | 12/1999 | Chudzik |
| 6,030,958 A | 2/2000 | Burns |
| 6,060,534 A | 5/2000 | Ronan |
| 6,096,018 A | 8/2000 | Luzio |
| 6,124,273 A | 9/2000 | Drohan |
| 6,133,325 A | 10/2000 | Schwartz |
| 6,156,572 A | 12/2000 | Bellamkonda |
| 6,174,999 B1 | 1/2001 | Miller |
| 6,184,266 B1 | 2/2001 | Ronan |
| 6,235,726 B1 | 5/2001 | Burns |
| 6,271,278 B1 | 8/2001 | Park |
| 6,294,202 B1 | 9/2001 | Burns |
| 6,334,968 B1 | 1/2002 | Shapiro |
| 6,368,356 B1 | 4/2002 | Zhong |
| 6,372,244 B1 | 4/2002 | Antanavich |
| 6,387,978 B2 | 5/2002 | Ronan |
| 6,410,044 B1 | 6/2002 | Chudzik |
| 6,425,918 B1 | 7/2002 | Shapiro |
| 6,500,777 B1 | 12/2002 | Wiseman |
| 6,511,650 B1 | 1/2003 | Eiselt |
| 6,521,223 B1 | 2/2003 | Calias |
| 6,548,081 B2 | 4/2003 | Sadozai |
| 6,566,345 B2 | 5/2003 | Miller |
| 6,599,526 B2 | 7/2003 | Dimitrijevich |
| 6,600,011 B2 | 7/2003 | McDonnell |
| 6,608,117 B1 | 8/2003 | Gvozdic |
| 6,610,669 B1 | 8/2003 | Calias |

(Continued)

FOREIGN PATENT DOCUMENTS

| | | |
|---|---|---|
| EP | 11806367 | 11/2007 |
| JP | 04-235124 | 8/1992 |

(Continued)

OTHER PUBLICATIONS

U.S. Patent and Trademark Office, Office Action mailed Mar. 27, 2013, in U.S. Appl. No. 12/919,667 ("Zawko").
Applicant's Reply to Office Action Mailed Mar. 27, 2013, filed via EFS on Jul. 18, 2013, in U.S. Appl. No. 12/919,667 ("Zawko").
U.S. Patent and Trademark Office, Notice of Allowance mailed Nov. 7, 2013, in U.S. Appl. No. 12/919,667 ("Zawko").
Shen, et al, "A Study on the Fabrication of Porous Chitosan/Gelatin Network Scaffold for Tissue Engineering", 2002, Polymer International, vol. 49, pp. 1596-1599.
U.S. Patent and Trademark Office, Office Action mailed Jun. 25, 2013 in U.S. Appl. No. 13/269,344 ("Schmidt")(pp. 7-8 describing how Schmidt includes a hydrogel having hyaluronic acid and cross-linked alginate).

(Continued)

*Primary Examiner* — Gina C Justice
*Assistant Examiner* — Genevieve S Alley
(74) *Attorney, Agent, or Firm* — Trop, Pruner & Hu, P.C.

(57) ABSTRACT

The present invention includes a hydrogel and a method of making a porous hydrogel by preparing an aqueous mixture of an uncrosslinked polymer and a crystallizable molecule; casting the mixture into a vessel; allowing the cast mixture to dry to form an amorphous hydrogel film; seeding the cast mixture with a seed crystal of the crystallizable molecule; growing the crystallizable molecule into a crystal structure within the uncrosslinked polymer; crosslinking the polymer around the crystal structure under conditions in which the crystal structure within the crosslinked polymer is maintained; and dissolving the crystals within the crosslinked polymer to form the porous hydrogel.

11 Claims, 13 Drawing Sheets

(56) References Cited

U.S. PATENT DOCUMENTS

| | | |
|---|---|---|
| 6,630,167 B2 | 10/2003 | Zhang |
| 6,630,457 B1 | 10/2003 | Aeschlimann |
| 6,638,917 B1 | 10/2003 | Li |
| 6,642,363 B1 | 11/2003 | Mooney |
| 6,653,240 B2 | 11/2003 | Crawford |
| 6,653,420 B2 | 11/2003 | Domschke et al. |
| 6,693,089 B1 | 2/2004 | Li |
| 6,703,041 B2 | 3/2004 | Burns |
| 6,723,709 B1 | 4/2004 | Pressato |
| 6,750,262 B1 | 6/2004 | Hahnle |
| 6,767,928 B1 | 7/2004 | Murphy |
| 6,793,675 B2 | 9/2004 | Shapiro |
| 6,818,018 B1 | 11/2004 | Sawhney |
| 6,841,153 B1 | 1/2005 | Chegini |
| 6,869,938 B1 | 3/2005 | Schwartz |
| 6,897,271 B1 | 5/2005 | Domschke |
| 6,913,765 B2 | 7/2005 | Li |
| 6,924,370 B2 | 8/2005 | Chudzik |
| 6,943,154 B2 | 9/2005 | Miller |
| 6,960,617 B2 | 11/2005 | Omidian |
| 6,991,652 B2 | 1/2006 | Burg |
| 7,022,313 B2 | 4/2006 | O'Connor |
| 7,083,697 B2 | 8/2006 | Dao |
| 7,201,917 B2 | 4/2007 | Malaviya |
| 7,235,295 B2 | 6/2007 | Laurencin |
| 7,347,988 B2 | 3/2008 | Hu |
| 2,008,026 A1 | 10/2008 | Vigh |
| 7,459,021 B2 | 12/2008 | Bukshpan |
| 7,553,903 B2 | 6/2009 | Riegel |
| 7,572,894 B2 | 8/2009 | Jin |
| 7,629,388 B2 | 12/2009 | Mikos |
| 7,682,540 B2 | 3/2010 | Boyan |
| 7,741,476 B2 | 6/2010 | Lebreton |
| 7,758,654 B2 | 7/2010 | Hoganson |
| 7,919,542 B2 | 4/2011 | Hudgins |
| 7,968,110 B2 | 6/2011 | Hubbard |
| 7,988,992 B2 | 8/2011 | Omidian |
| 7,989,505 B2 | 8/2011 | Hu |
| 7,998,380 B2 | 8/2011 | Turng |
| 8,025,901 B2 | 9/2011 | Kao |
| 8,110,242 B2 | 2/2012 | Hawkins |
| 8,133,840 B2 | 3/2012 | Mika |
| 8,323,675 B2 | 12/2012 | Greenawalt |
| 2002/0131933 A1 | 9/2002 | Delmotte |
| 2003/0134132 A1 | 7/2003 | Winterton |
| 2004/0138329 A1 | 7/2004 | Hubbell |
| 2005/0107868 A1 | 5/2005 | Nakayama |
| 2006/0173394 A1* | 8/2006 | Stroock et al. ............ 602/41 |
| 2007/0026038 A1* | 2/2007 | Bayer et al. ............ 424/423 |
| 2007/0031498 A1 | 2/2007 | Zong |
| 2007/0202084 A1 | 8/2007 | Sadozai |
| 2008/0069857 A1 | 3/2008 | Yeo |
| 2008/0182012 A1 | 7/2008 | Fisher |
| 2008/0292664 A1 | 11/2008 | Giammona |
| 2009/0062233 A1 | 3/2009 | Ji |
| 2009/0081265 A1 | 3/2009 | Peppas |
| 2009/0170973 A1 | 7/2009 | Mattiasson |
| 2010/0062232 A1 | 3/2010 | Schauer |
| 2010/0273667 A1 | 10/2010 | Kotov |
| 2011/0008442 A1 | 1/2011 | Zawko |
| 2012/0039959 A1 | 2/2012 | Tessmar |
| 2012/0282302 A1 | 11/2012 | McCanless |

FOREIGN PATENT DOCUMENTS

| | | |
|---|---|---|
| JP | 06100468 | 9/1992 |
| JP | 06-100468 | 12/1994 |
| JP | 04235124 | 5/1995 |
| JP | 20000027821 | 2/2000 |
| JP | 2003062057 | 8/2001 |
| JP | 2001212224 | 12/2001 |
| JP | 3805654 B | 5/2006 |
| KR | 20020027747 | 4/2002 |
| KR | 20020032351 | 5/2002 |
| KR | 20030055102 | 7/2003 |
| WO | 9739737 | 10/1997 |
| WO | 02092678 | 11/2002 |
| WO | 2005020849 A2 | 3/2005 |
| WO | 2009108760 A2 | 3/2009 |

OTHER PUBLICATIONS

Cho, W.J., et al. "Alginate Film as a Novel Post-Surgical Tissue Adhesion Barrier", Journal of Biomaterials Science-Polymer Edition, 21 (6-7), p. 701-713, 2010.

Oerther, S., et al. "Hyaluronate-Alginate Gel as a Novel Biomaterial: Mechanical Properties and Formation Mechanism", Biotechnology Bioeng., 63, 2006-215, 1999.

International Search Report and Written Opinion for PCT/US2011/055461, dated Dec. 1, 2011, 10 pages.

Lindenhayn, K., et al., "Retention of Hyaluronic Acid in Alginate Beads: Aspects for in vitro Cartilage Engineering," J. Biomed. Mater. Res., (1999), vol. 44, pp. 149-155.

Masters, Kristyn S., et al., "Designing Scaffolds for Valvular Interstitial Cells: Cell Adhesion and Function on Naturally Derived Materials," J. Biomed. Mater Res. 71A, (2004), pp. 172-180.

Miralles, G., et al., "Sodiom Alginate Sponges With or Without Sodium Hyaluronate: In Vitro Engineering of Cartilage," J. Biomed. Mater. Res., (2001), vol. 57, pp. 268-278.

Zawko, Scott A., et al., "Crystal Templating Dendritic Pore Networks and Fibrillar Microstructure into Hydrogels," Acta Biomaterials, (2010), vol. 6, pp. 2415-2421.

Oerther, S., et al., "High Interaction Alginate-Hyaluronate Associations by Hyaluronate Deacetylation for the Preparation of Efficient Biomaterials," Biopolymers, 54: 273-281, 2000.

U.S. Appl. No. 13/269,344, filed Oct. 7, 2011, entitled "Anti-Adhesive Barrier Membrane Using Alginate and Hyaluronic Acid for Biomedical Applications" by Sarah Mayes.

U.S. Appl. No. 13/269,366, filed Oct. 7, 2011 entitled "One-Step Processing of Hydrogels for Mechanically Robust and Chemically Desired Features" by Sarah Mayes.

Bekkers, John M., et al., "Targeted Dendrotomy Reveals Active and Passive Contributions of the Dendritic Tree to Synaptic Integration and Neuronal Output," PNAS, Jul. 3, 2007, vol. 104, No. 27, pp. 11447-11452.

Brisken, Cathrin, et al., "Alveolar and Lactogenic Differentiation," J. Mammary Gland Biol. Neoplasia, (2006), 11:239-248.

Chung, Cindy, et al., "Effects of Auricular Chondrocyte Expansion on Neocartilage Formation in Photocrosslinked Hyaluronic Acid Networks," Tissue Eng., Sep. 2006, 12(9):2665-2673.

Duffy, David C., et al., "Rapid Prototyping of Microfluidic Systems in Poly(dimethylsiloxane)," Anal. Chem., (1998), 70:4974-4984.

International Search Report and Written Opinion for PCT/US2009/035257, dated Oct. 12, 2009, 12 pages.

Khademhosseini, Ali, et al., "Microscale Technologies for Tissue Engineering and Biology," PNAS, Feb. 21, 2006, vol. 103, No. 8, pp. 2480-2487.

King, Kevin R., et al., "Biodegradable Microfluidics," Adv. Mater., Nov. 18, 2004, vol. 16, No. 22, pp. 2007-2012.

Larina, Olga, et al., "Ca2+ Dynamics in Salivary Acinar Cells: Distinct Morphology of the Acinar Lumen Underlies Near-Synchronous Global Ca2+ Responses," Journal of Cell Science, 118:4131-4139.

Leach, Jennie Baier, et al., "Photocrosslinked Hyaluronic Acid Hydrogels: Natural, Biodegradable Tissue Engineering Scaffolds," Biotechnol. Bioeng. 82:578-259.

Ma, Peter X., et al., "Biodegradable Polymer Scaffolds with Well-Defined Interconnected Spherical Pore Network," Tissue Engineering, vol. 7, No. 1, (2001), pp. 23-39.

Oaki, Yuya, et al., "Experimental Demonstration for the Morphological Evolution of Crystals Grown in Gel Media," Crystal Growth & Design, Jun. 27, 2003, vol. 3, No. 5, pp. 711-716.

Peppas, N.A., et al., "Hydrogels in Pharmaceutical Formulations," European Journal of Pharmaceutics and Biopharmaceutics, (2000), 50, pp. 27-46.

(56) References Cited

OTHER PUBLICATIONS

Shah, Mita M., et al., "Branching Morphogenesis and Kidney Disease," Development 131, (2004), pp. 1449-1462.

Tsang, Valerie Liu, et al., "Fabrication of 3D Hepatic Tissues by Additive Photopatterning of Cellular Hydrogels," The FASEB Journal, (2007), 21, pp. 790-801.

Uludag, Hasan, et al., "Technology of Mammalian Cell Encapsulation," Advanced Drug Delivery Reviews, (2000), 42:29-64.

Xu, An-Wu, et al., "Biomimetic Mineralization," J. Mater. Chem., (2007); 17, pp. 415-449.

Yang, Shoufeng, et al., "The Design of Scaffolds for Use in Tissue Engineering. Part II. Rapid Prototyping Techniques," Tissue Engineering, (2002), vol. 8, No. 1, 11 pages.

Huang, "Rapid Fabrication of Bio-inspired 3D Microfluidic Vascular Networks", Advanced Materials, Jul. 10, 2009, 3567-3571, vol. 21, WILEY-VCH, Weinheim.

Depierro, "Influence of Polymerization Conditions on Nanostructure and Properties of Polyacrylamide Hydrogels Templated from Lyotropic Liquid Crystals", Chemical Materials, Oct. 18, 2006, 5609-5617, vol. 18, No. 23, American Chemical Society, Iowa City, Iowa.

Huang, "Rapid Fabrication of 3-D Branched Microvascular Flow Networks", Twelfth International Conference on Miniaturized Systems for Chemistry and Life Sciences, Oct. 12-16, 2008, 1435-1437, San Diego, California.

Seidel, "Synthesis of PolyHEMA Hydrogels for Using as Biomaterials. Bulk and Solution Radical-Initiated Polymerization Techniques", Materials Research, vol. 3, No. 3, Jul. 2000, 8 pages.

* cited by examiner

US 8,728,499 B2

DENDRITIC MACROPOROUS HYDROGELS PREPARED BY CRYSTAL TEMPLATING

This application is a continuation of U.S. patent application Ser. No. 12/919,667, filed Aug. 26, 2010 and entitled "DENDRITIC MACROPOROUS HYDROGELS PREPARED BY CRYSTAL TEMPLATING", which claims priority to Patent Cooperation Treaty Application Serial No. PCT/US2009/035257, filed Feb. 26, 2009 and entitled "DENDRITIC MACROPOROUS HYDROGELS PREPARED BY CRYSTAL TEMPLATING", which claims priority to U.S. Provisional Patent Application Ser. No. 61/031,651, filed Feb. 26, 2008. The content of each of the above applications is hereby incorporated by reference.

STATEMENT OF FEDERALLY FUNDED RESEARCH

This invention was made with U.S. Government support under Contract No. BES-021744 and BES-0500969 awarded by the NSF. The government has certain rights in this invention.

BACKGROUND

The present invention relates in general to the field of hydrogels, and more particularly, to dendritic macroporous hydrogels prepared by crystal templating.

Without limiting the scope of the invention, its background is described in connection with hydrogels. Hydrogels are generally polymer chain networks that are water-insoluble, but that absorb water. Often described as being "superabsorbent," hydrogels are able to retain up to 99% water and can be made from natural or synthetic polymers. Often, hydrogels will have a high degree of flexibility due to their high water content. Common uses for hydrogels include: sustained drug release, as scaffolds (e.g., in tissue engineering), as a thickening agent, as a biocompatible polymer, in biosensors and electrodes and for tissue replacement applications. Natural hydrogels may be made from agarose, methylcellulose, hyaluronic acid (HA), and other naturally-derived polymers.

One method for making hydrogels is taught by U.S. Pat. No. 7,307,132, issued to Nestler, et al., for a method of producing low-odor hydrogel-forming polymers. Briefly, a low-odor hydrogel-forming acrylic acid polymer is prepared by preparing a polymeric hydrogel by free-radically polymerizing a monomer composition comprising at least 50% by weight of acrylic acid in an aqueous polymerization medium and converting said hydrogel into a particulate hydrogel or into hydrogel-forming powder; and optionally treating the particulate hydrogel or said hydrogel-forming powder with a crosslinking substance which, actually or latently, contain at least two functional groups capable of reacting with the carboxyl groups on the addition polymer; characterized by the acrylic acid used in step (a) containing less than 400 ppm of acetic acid and propionic acid.

Another method is taught by U.S. Pat. No. 6,943,206, issued to Haraguchi for an organic/inorganic hybrid hydrogel and method for manufacturing. Briefly, an organic/inorganic hybrid hydrogel is said to have superior homogeneity, transparency, mechanical properties, and swelling and shrinking properties. A dry body of the organic/inorganic hybrid hydrogel is obtained by removing water from said hydrogel. The organic/inorganic hybrid hydrogel comprises a water soluble polymer (A), a water swelling clay mineral (B) which can be homogeneously dispersed in water, and water (C), and water (C) is included in a three-dimensional network formed by (A) and (B).

BRIEF DESCRIPTION OF THE DRAWINGS

For a more complete understanding of the features and advantages of the present invention, reference is now made to the detailed description of the invention along with the accompanying figures and in which:

FIG. 2A) polarized light microscopy image of uncrosslinked HA hydrogel-urea crystal composite; (FIG. 2B) phase contrast microscopy image of uncrosslinked HA hydrogel-urea crystal composite; (FIG. 2C) phase contrast microscopy image of crosslinked HA hydrogel after removal of the urea crystals; (FIG. 2D) polarized light microscopy image of uncrosslinked HA hydrogel-urea crystal composite; (FIG. 2E) phase contrast microscopy image of uncrosslinked HA hydrogel-urea crystal composite; and (FIG. 2F) phase contrast microscopy image of crosslinked HA hydrogel after removal of the urea crystals;

(FIG. 3A) time lapse series of the urea crystal front captures with video Brightfield microscopy; (FIG. 3B) atomic force microscopy (AFM) image of the surface of a rinsed urea-templated HA hydrogel in air; and (FIG. 3C) profile of the AFM image perpendicular to the orientation of the ridges;

(FIG. 4A) three separate nucleation points producing a hydrogel with three radial patterns; (FIG. 4B) line nucleation points producing a hydrogel with linear alignment of crystals; and (FIG. 4C) magnified view of FIG. 4B. Scale bars are 1000 .mu.m (FIGS. 4A and 4B) and 100 .mu.m (FIG. 4C);

(FIG. 5A) photograph of scaled-up free standing films of plain and urea-templated HA and alginate; (FIG. 5B) top down view of the scanning electron microscopy images (SEM) of crystal templated HA after cross-linking and rinsing; (FIG. 5C) portion of the film curled back to expose crevices in the hydrogel created by urea crystals; (FIG. 5D) cross-section of the hydrogel perpendicular to the pore orientation; (FIG. 5E) parallel cross-section depicting the fibrillar morphology; and (FIG. 5F) magnified view of image of FIG. 5E; (FIG. 6A) urea crystal and alginate; (FIG. 6B) urea crystal and 4-arm-PEG acrylate; (FIG. 6C) urea crystal and chitosan; (FIG. 6D) potassium phosphate crystal and hyaluronic acid; (FIG. 6E) b-cyclodextrin crystal and alginate; and (FIG. 6F) magnified image of b-cyclodextrin crystals and alginate. Scale bars are 1000 .mu.m (FIGS. 6A to 6E) and 100 .mu.m (FIG. 6F).

DETAILED DESCRIPTION

Figure 1:
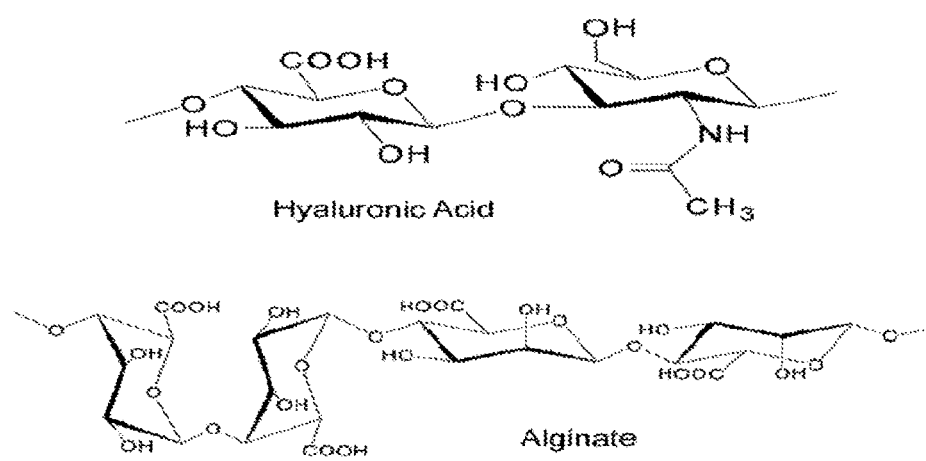
FIG. 1 shows the chemical structures of biopolymers used in these hydrogels and a schematic of the crystal-templating technique.
Figure 1:
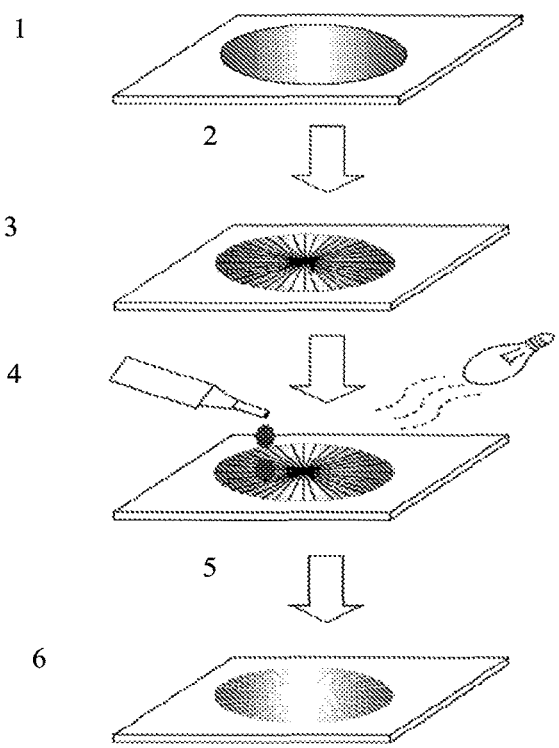

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The creation of macroporosity within tissue engineering scaffolds is important because it influences cellular infiltration, scaffold remodeling, nutrient diffusion, vascular in-growth and functional integration with native tissues. The present inventors have developed a novel crystal-templating technique to fabricate hydrogels with continuous dendritic porous networks. No other current method is capable of creating such scaffolds. Additional advantages of this technique are that it is compatible with natural biomaterials, it is fast, can be scaled up, and does not require any expensive equipment or reagents. Crystal-templating works by growing a dendritic crystal template within a solution of uncrosslinked biopolymer, crosslinking the biopolymer around the template, and removing the crystals by washing with water. The result is a macroporous hydrogel with a network of pores matching the shape of the crystal template. We have used urea crystal templates to pattern photocrosslinked HA and calcium-crosslinked alginate hydrogels. The crystal-templating technique and the materials created by it address the challenge of fabricating materials with intricate dendritic microarchitecture that is observed in native tissues.

The goal of tissue engineering is to create materials that can replace or repair injured tissue. To that end it is desirable to have tissue engineered constructs that mimic the microarchitecture of native tissues. An important structural feature of many tissues is highly branched networks of vessels and ducts. Examples are the bronchioles, the microvasculature, lymphatic vessels, the ductal networks of salivary gland, mammary gland, and kidney, and the dendritic trees produced by neurons [1-4]. Such networks exhibit branching, multiple length scales, a directional orientation, and three-dimensionality. A tissue may contain multiple entwined networks; for example, bronchioles, arterial vessels, and venous vessels within the lungs. Although many techniques are available for creating porosity within tissue engineered constructs they fall short of reproducing even one such network [5].

Briefly, current techniques available for creating porosity are gas-foaming, lyophilization, thermally-induced phase separation and porogen leaching of salts and un-crosslinked polymer microspheres [6-8]. Soft replica molding can transfer patterns from etched silicon to polymers such as poly (lactide-co-glycolide), however this is a two-dimensional technique and the stacked layers are a poor approximation of three-dimensional porosity [9-10]. The advantages of these methods are that they are easy to implement and scale-up. The disadvantage is that they provide little control over pore morphology and limited compatibility with natural materials. Rapid prototyping techniques permit precise control over pore morphology through the use of computer-aided design systems [11-13]. Rapid prototyping is suitable for creation of square and hexagonal lattices but not for the complex three-dimensional dendritic patterns observed in native tissues. Although rapid prototyping techniques are compatible with synthetic polymers they are not as suitable for natural materials which are water soluble and viscous. A further limitation is that the resolution of such techniques is larger than the length scale of individual cells and neuronal processes. Scaffolds depicted in the literature typically have features hundreds of microns in length which are too large to precisely guide cellular infiltration. Fabrication of three-dimensional multilayer constructs can be impractical because each scaffold must be built layer by layer with costly equipment.

Hydrogel scaffolds are uniquely suited for tissue engineering applications because they more closely resemble natural tissues with respect to mechanical properties, porosity, and water content than do other materials [14]. In particular, polysaccharides, such as hyaluronic acid (HA) and sodium alginate (SA) are attractive materials because they are composed of the same chemical constituents as native extracellular matrix components. They also exhibit excellent biocompatibility and non-immunogenicity. HA has found use as a dermal filler, adhesion barrier, intra-articular viscosupplement, vitreal substitute, drug delivery matrix and tissue engineering scaffold for cartilage, skin, adipose and vocal cord [15-21]. Alginate has been used extensively for cell encapsulation, drug delivery and tissue engineering of adipose and cartilage [22-24].

In comparison to synthetic materials, these polysaccharides are considerably more difficult to work with because they have high molecular weights, are polydisperse, organic insoluble, pH and temperature sensitive, and produce viscous solutions even at dilute concentrations. Thus, it is a challenge to create tissue engineered scaffolds with biomimetic porous networks in HA and SA hydrogels. To address this problem the present invention describes a crystal-templating technique that uses in situ crystallization to carve out pores within biopolymer hydrogels. Salts and small organic molecules can precipitate as crystalline branching networks under certain conditions. The similarity between such networks and the dendritic patterns of microvasculature and neuronal dendritic trees prompted us to use in situ crystallization to template biopolymer hydrogels with macroporous networks. SA and HA are both linear, unbranched, anionic, high molecular weight polysaccharides (their chemical structures are depicted in FIG. 1), however they are distinguished by their mode of crosslinking HA can be crosslinked by derivatization with methacrylate side chains and exposure to UV light and a photoinitiator [25]. Alginate can be crosslinked by addition of divalent cations which crosslink adjacent guluronic acid blocks [24]. Both modes of crosslinking are compatible with the crystal-templating technique of the present invention. Urea was chosen as the crystallite because of its high water solubility and propensity for extensive hydrogen bonding to permit interaction with biopolymer chains in solution.

The method described in the present invention includes five steps: film casting, solvent evaporation, crystal growth, crosslinking, and rinsing. These steps are depicted in FIG. 1. Small droplets (.about.2 .mu.L) of biopolymer and urea were cast onto microscope slides. The droplets were evaporated at .about.50% relative humidity to produce thin hydrated films of about 5 mm in diameter on microscope slides. Solvent evaporation is required to achieve the super-saturation conditions necessary for crystallization. Evaporation also greatly increases the biopolymer concentration and solution viscosity. The combination of high viscosity and hydrogen bonding suppresses spontaneous urea crystallization and facilitates super-saturation. Urea seed crystals were deposited on the tips of a fine pair of tweezers and applied to the centers of each HA/urea and SA/urea film. Crystal growth began immediately and produced long dendritic branches that extended from the center to the edge of the film. Within seconds the entire volume of the hydrogel films were filled with urea crystals. These crystals comprised the urea crystal template.

FIG. 1 shows the chemical structures of biopolymers used in these hydrogels and schematic of the crystal-templating technique. Crystal templated hydrogels were created by casting solution of biopolymer and urea, e.g., hyaluronic acid and alginate. The solvent was evaporated to achieve supersaturation conditions concentrations of urea. As seen in 1 the biopolymer-urea droplet is added to the glass slide, followed by drying 2. Resulting in the application of a seed crystal to the center of the film nucleated crystallization as seen in 3. Following crystallization the biopolymer is crosslinked by either UV or calcium 4. A water rinse 5 removes the urea crystals leaving behind a macroporous hydrogel templated 6 with the pattern of the urea crystals.

After the completion of the crystallization the films were crosslinked by either UV exposure or calcium as appropriate. Both methods of crosslinking are rapid and accurately preserve the configuration of the crystal template. After crosslinking the crystals were easily removed with water. The end products were hydrogels with dendritic macroporous networks. Crystal-templated HA hydrogels are shown in FIG. 2. These thin films are easily observable by transmission light microscopy. Droplets containing both biopolymer and urea crystals (i.e., biopolymer-urea "composites") were highly birefringent when observed through crossed polarizers. These composite films exhibited a characteristic maltese cross pattern indicative of radial alignment. The colors of the composites in polarized light appeared to correspond to film thickness; the films were thickest at the center and thinned out toward the edges. After crosslinking and rinsing, the hydrogels lost most of their birefringence and exhibited only a faint white color when viewed through crossed polarizers. The hydrogel morphology consisted of aligned straight "fibrils" that were the inverse shape of the crystal template.

Figure 2A:
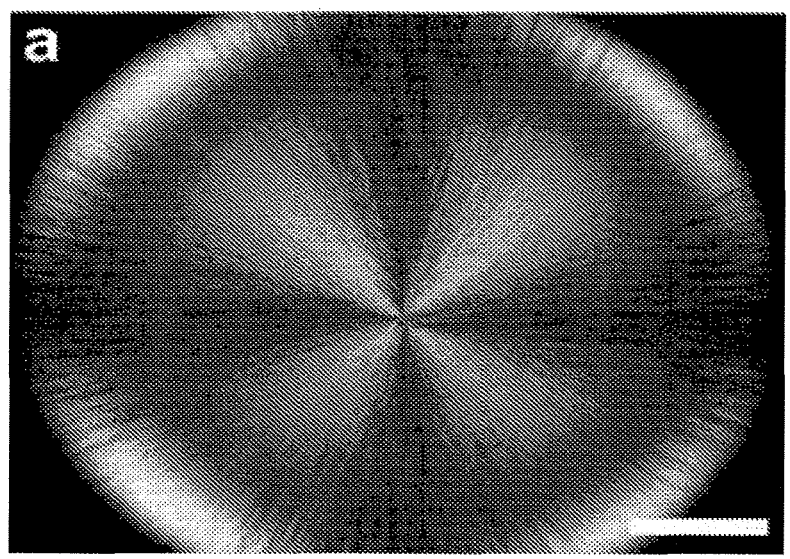
FIGS. 2A to 2F are polarized light (FIGS. 2A and 2D) and phase contrast (FIGS. 2B, 2C, 2E, and 2F) microscopy images of crystal templated HA hydrogel.
Figure 2B:
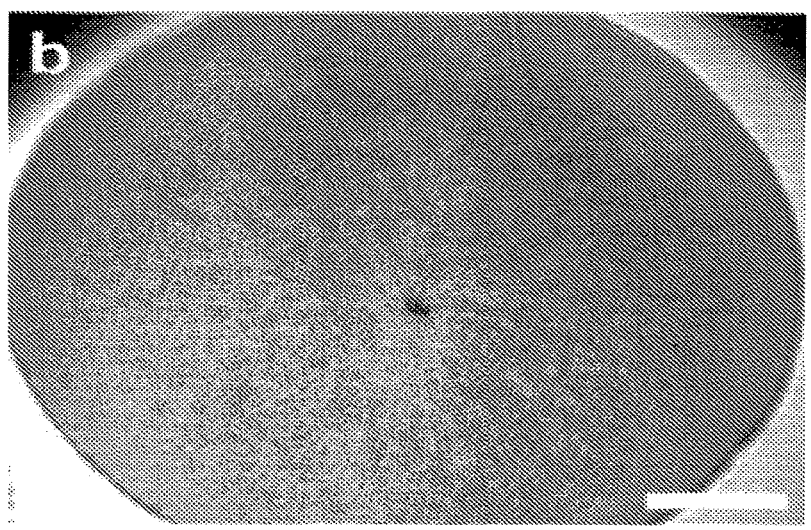
Figure 2C:
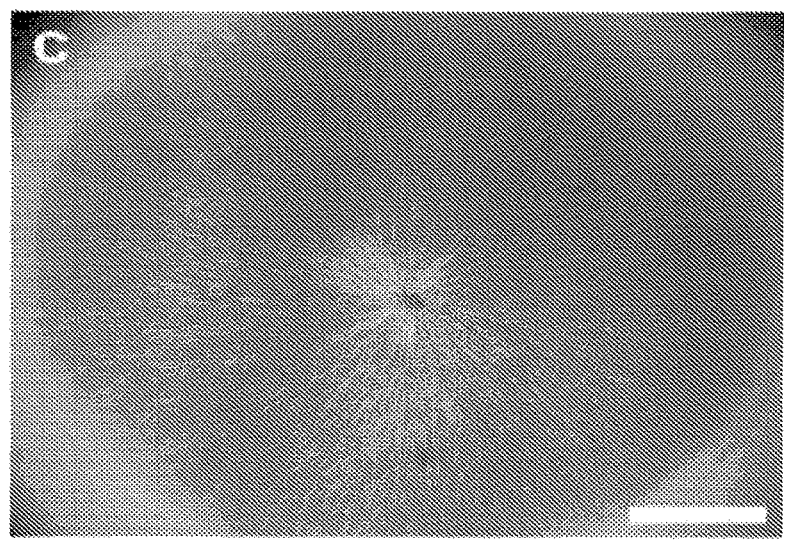
Figure 2D:
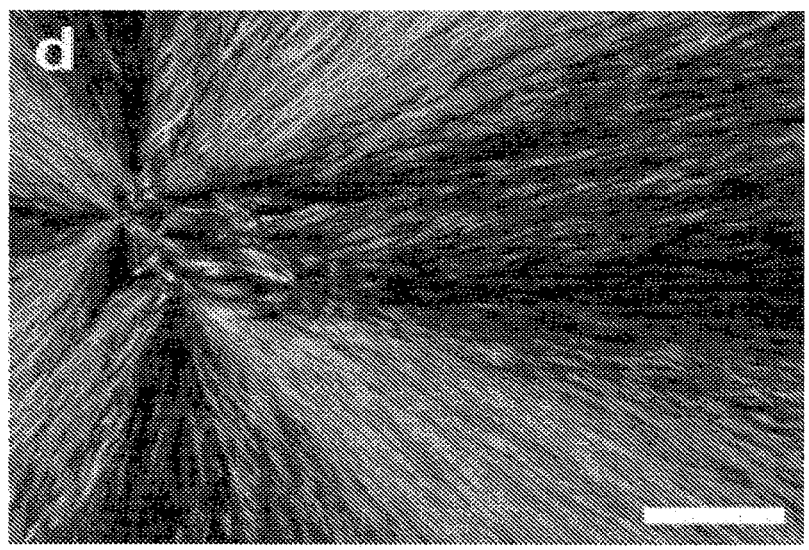
Figure 2E:
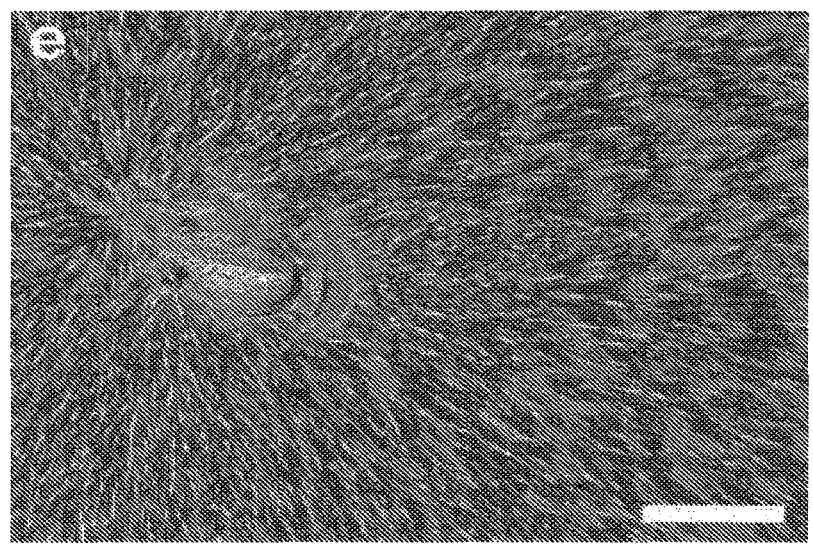
Figure 2F:
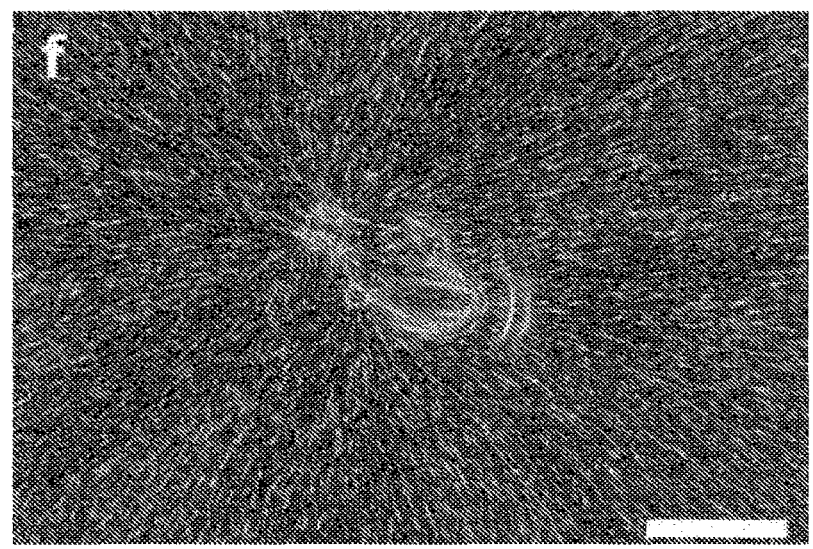

FIGS. 2A to 2F are polarized light (FIGS. 2A and 2D) and phase contrast (FIGS. 2B, 2C, 2E, and 2F) microscopy images of crystal templated HA hydrogel. FIGS. 2A to 2D are images of the uncrosslinked hydrogel-crystal composite. FIGS. 2E and 2F images of the hydrogels after crosslinking and removal of the urea crystals. Crystal growth was nucleated at the center of each hydrogel and grew radially outward toward the edge of the hydrogel. The hydrogel-crystal composites in the first column exhibit a maltese cross characteristic of alignment. The crystal template pattern was retained by the hydrogel after crosslinking and rinsing. Scale bars are 1000 .mu.m in FIGS. 2A to 2C and 100 .mu.m in FIGS. 2D to 2F.

Figure 3A:
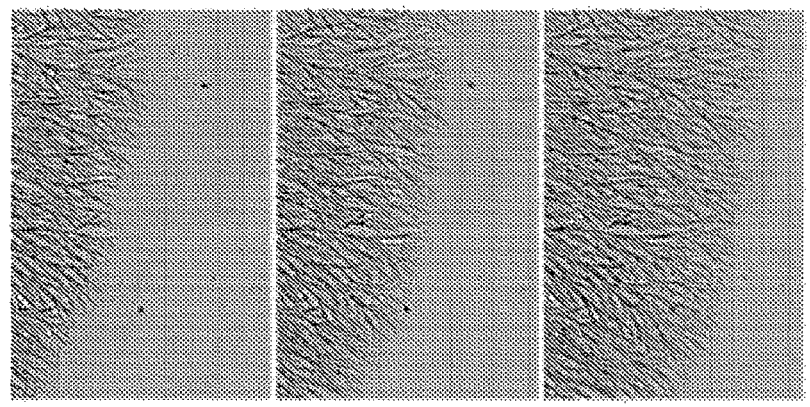
FIGS. 3A to 3C are high magnification images of urea crystals and templated HA hydrogels.
Figure 3B:
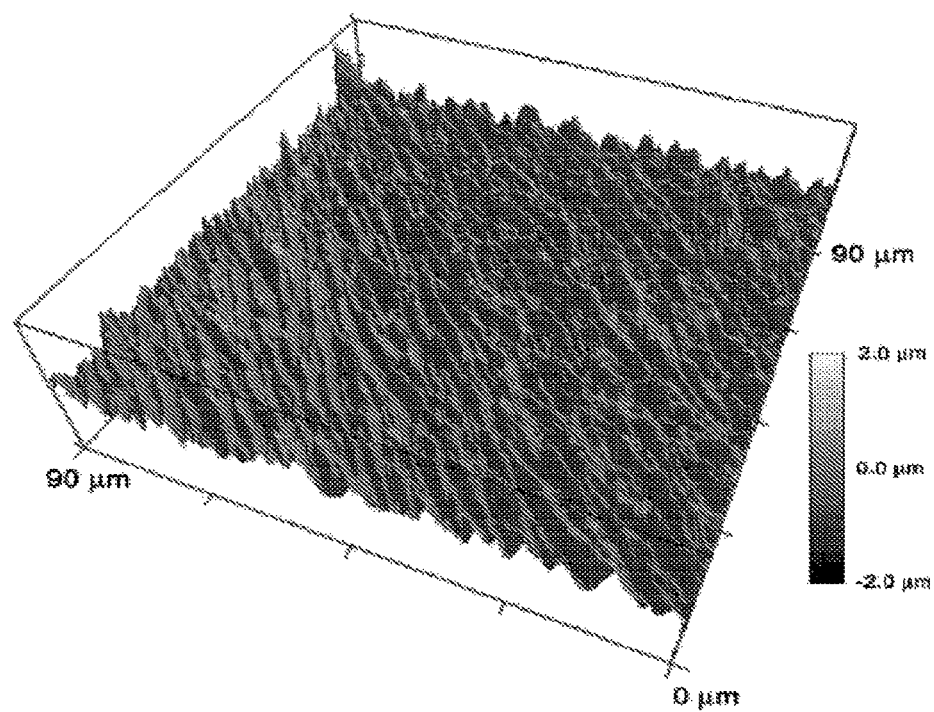
Figure 3C:
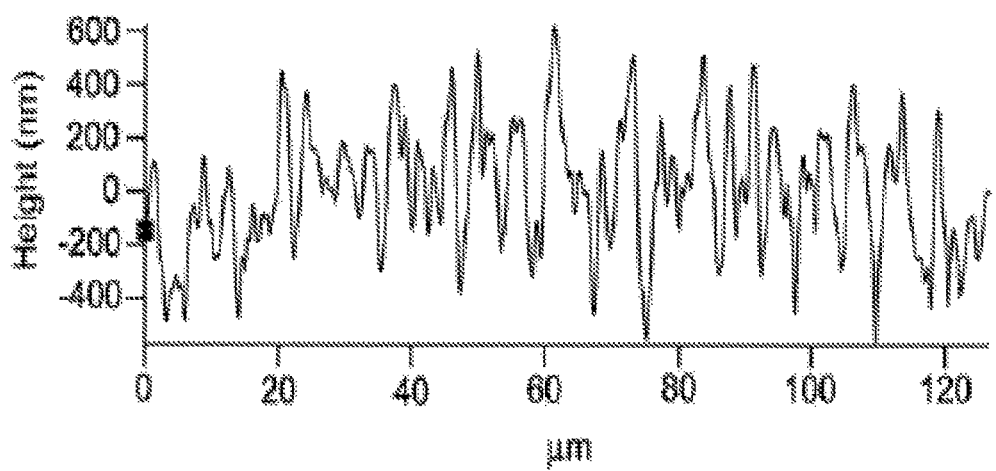

Images of urea crystal growth were captured using video microscopy. FIG. 3A depicts high magnification images of a growing urea crystal front. FIGS. 3A to 3C are high magnification images of urea crystals and templated hyaluronic acid hydrogels. FIG. 3A is a time lapse series of the urea crystal front captured with video Brightfield microscopy. Images are five seconds apart. Scale bar=10 .mu.m. FIG. 3B is an AFM image of the surface of a rinsed urea-templated HA hydrogel in air. The ridges correspond to the HA hydrogel. The grooves between the ridges had contained urea crystals that were washed out. This image demonstrates that HA hydrogel was templated by the crystallization of urea. FIG. 3C shows a profile of the AFM image perpendicular to the orientation of the ridges.

It was found that the crystals were thin tightly packed needles that sprouted a high density of branches. As the urea branches approached neighboring crystals the local concentration of urea became depleted and branch growth was terminated; therefore, the longest continuous branches were those that grew in the most radial direction away from the point of nucleation. Direct observation of crystal growth confirmed that the crystals grew continuously; therefore, we conclude that the porous network within the crystal-templated hydrogels is also continuous.

Branches were not observed when urea crystals were grown in the absence of biopolymer which indicates the importance of viscosity to induction of dendritic growth. Such an effect has been observed by others that have examined crystal growth in the presence of polymers [26, 27]. We found that the growth rate was highly dependent on the ratio of urea to HA concentrations. This ratio was adjusted by fixing the HA concentration at 10 mg/mL and varying the urea concentration from 2.5 to 180 mg/mL. Crystal growth could not be nucleated for a ratio of 0.25. For increasing ratios, the growth rate also increased and reached a rate of 1000 .mu.m/sec for a ratio of 6. For ratios of 8 and greater a viscous liquid was expelled from the crystals shortly after crystallization. This liquid was easily visible under polarized light as dark liquid on the surface of the birefringent urea crystals. The liquid was likely rich in HA and photoinitiator which are impurities with respect to urea crystals. At higher ratios the urea crystals became increasingly more tightly packed and less branched. Bulk polyhedral urea crystals were observed on the surface of the needle crystals when the ratio was 18. We concluded that ratios of 6 and under were most effective at templating the biopolymer because this ensured that the hydrogel was templated by the crystals rather than excluded from the template.

The micro-topography of a rinsed urea-templated HA hydrogel was observed by contact mode AFM in air (FIG. 3B). The surface of the hydrogel consisted of alternating parallel valleys and ridges. The valleys were carved out by the growth of urea crystals. During crystallization, the crystal front expels the biopolymer as an impurity. Thus, the biopolymer was compressed into the interstices between urea crystals and formed the radially aligned thin ridges. A profile of the hydrogel perpendicular to the length of the ridges is shown in FIG. 3C. The dimensions of these ridges, less than 1 .mu.m in height and spaced between 1 and 2 .mu.m apart, are consistent with our observations under the light microscope in FIG. 3A.

Urea crystal growth can be nucleated two ways. Spontaneous nucleation occurs when the concentration of urea exceeds a critical super-saturation. Typically, spontaneous nucleation occurred on the edges of the hydrogels. Hydrogels never had more than one spontaneous nucleation event because crystal growth was very rapid.

Figure 4A:
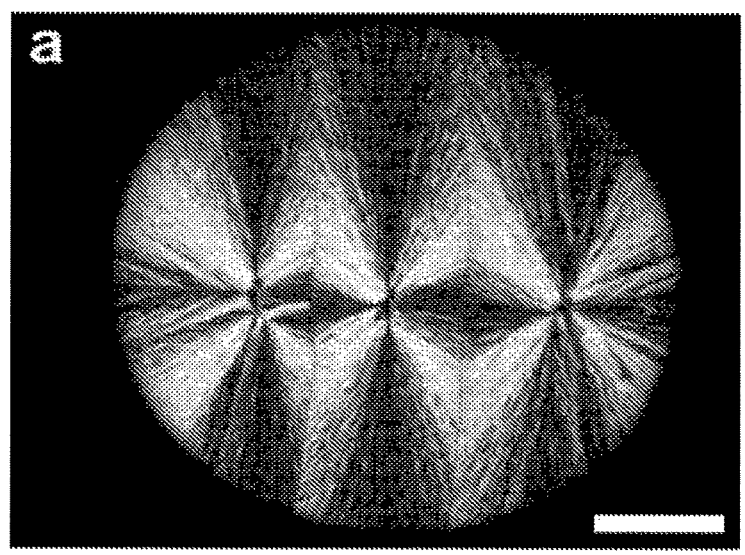
FIGS. 4A to 4C show the urea seed crystal technique used to control the morphology of crystals and pores within HA hydrogels.
Figure 4B:
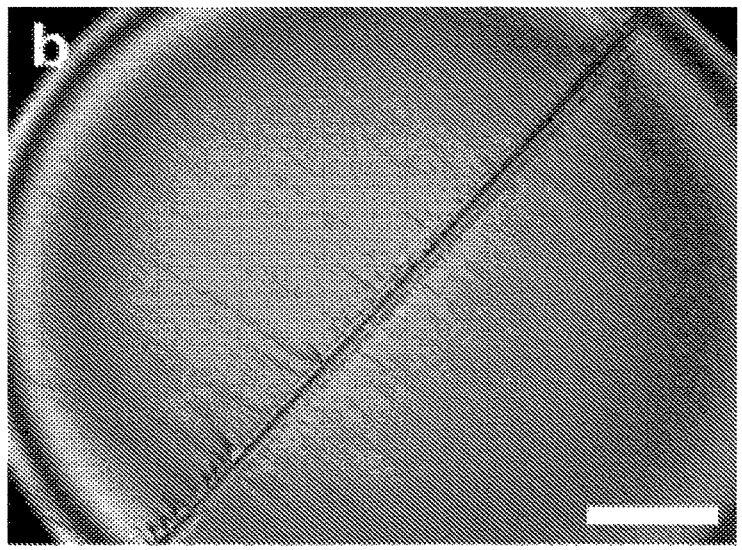
Figure 4C:
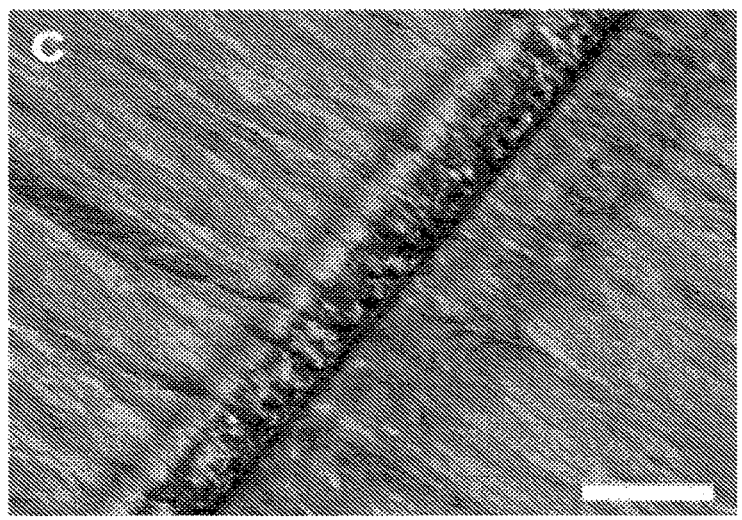

FIGS. 4A to 4C show that the urea seed crystal technique can be used to control the morphology of crystals and pores within HA hydrogels. FIG. 4A shows three separate nucleation points produced a hydrogel with three radial patterns. FIG. 4B shows a line of nucleation points produced a hydrogel with linear alignment of crystals. FIG. 4C shows a magnified image of FIG. 4B. Scale bars are 1000 .mu.m (FIG. 4A and FIG. 4B) and 100 .mu.m (FIG. 4C).

Applying a seed crystal to initiate urea crystal growth was a simple method for controlling the macro-morphology structure of the crystal template. This was done in conditions that suppressed spontaneous nucleation by partially drying the hydrogel droplets under humid conditions. At equilibrium under humid conditions the hydrated films have a concentration of urea great enough to sustain crystal growth but too low for spontaneous nucleation. Un-nucleated hydrogel films could be maintained for days until the introduction of a seed crystal. This permits selection of both the time and location of the nucleation. Films produced by the application of one seed in the center of the film are depicted in FIG. 2. Application of three seeds produced the three domain template in FIG. 4A. Individual seeds produced radial crystal growth, whereas a line of seeds produced parallel alignment throughout the hydrogel film (FIG. 4B). Thus, seed nucleation is a simple method for engineering template morphology.

The droplets deposited on microscope slides formed thin films a few microns thick as estimated by electron microscopy. Crosslinked films could be released from the surfaces of the microscope slides by agitation and transferred to solution for storage if desired. These films remained intact and did not fall apart, but could be enzymmatically degraded by hyaluronidase and dissolved by treatment with a calcium chelator, EDTA. Scale-up of the urea-templating procedure was accomplished for both HA and SA using a procedure similar to that used for the droplets. The scaled-up films were prepared by casting 2.6 mL of solution into 12-well plates with diameters of 2.2 cm per well. Three to four days were required to evaporate solvent. Crystal growth could be nucleated both spontaneously and by seed crystal.

Figure 5A:
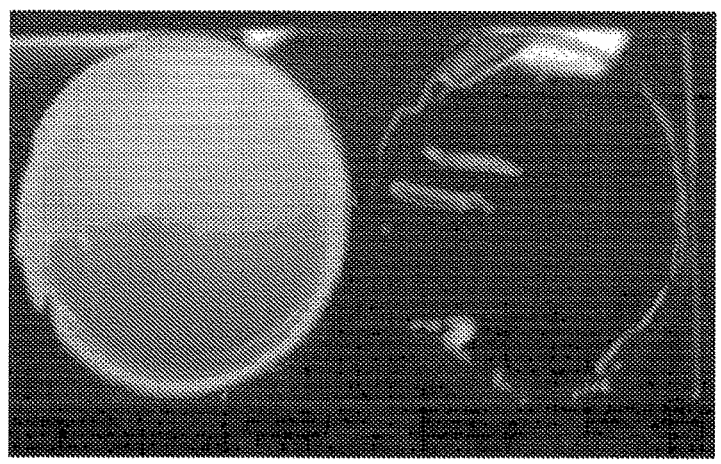
FIGS. 5A to 5F shows the process of urea-templating scaled up from droplets to thick films.
Figure 5B:
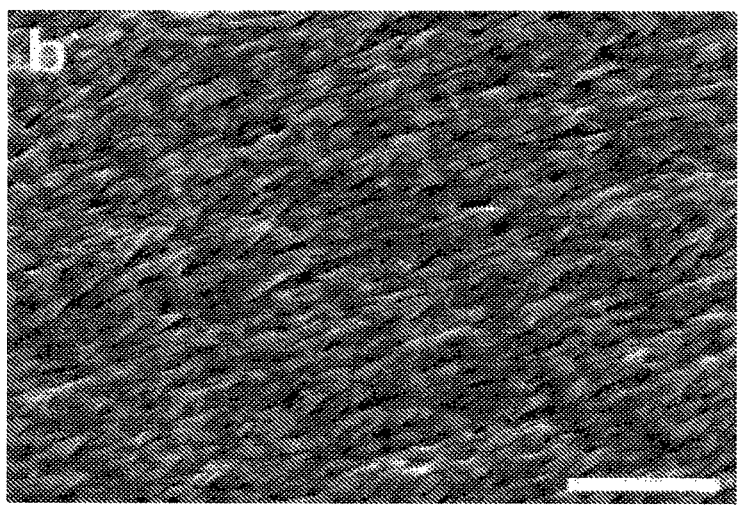
Figure 5C:
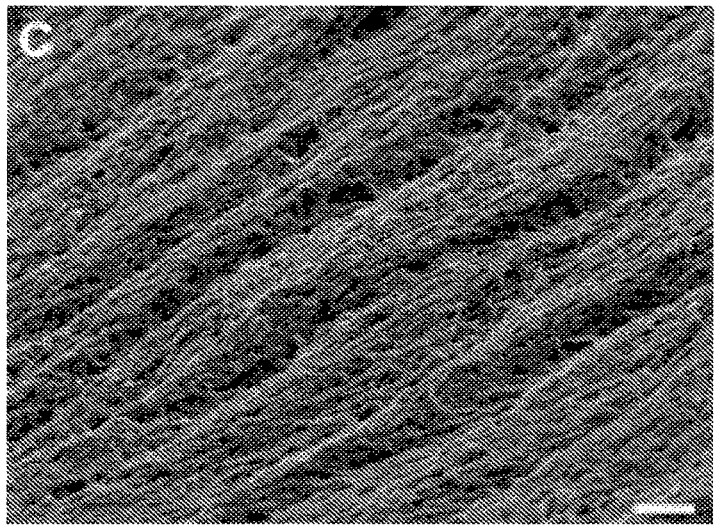
Figure 5D:
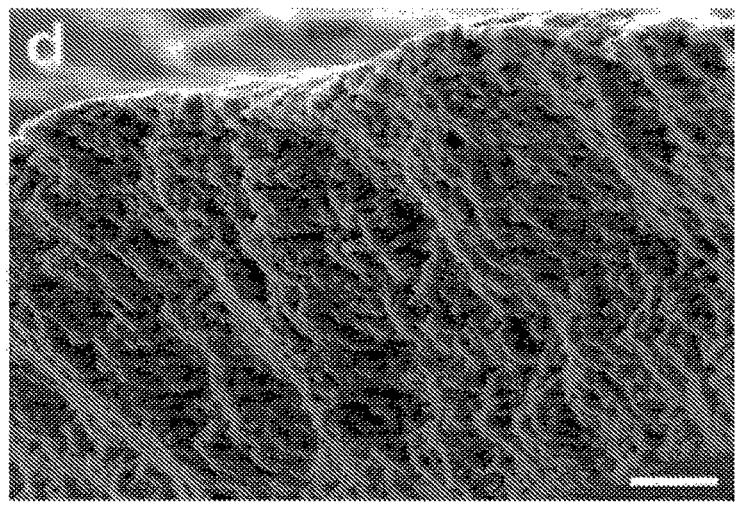
Figure 5E:
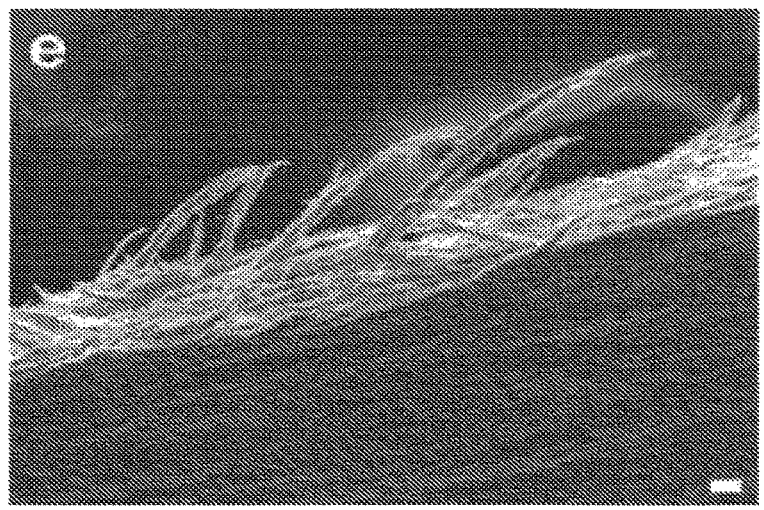
Figure 5F:
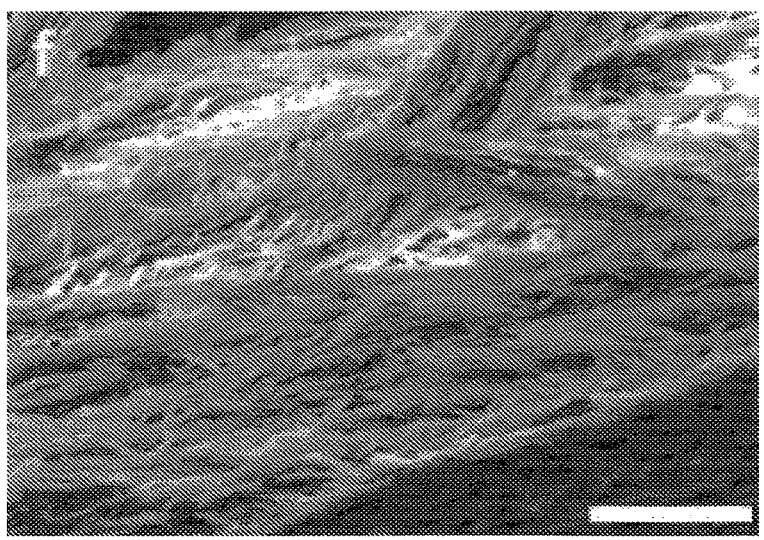
Figure 6A:
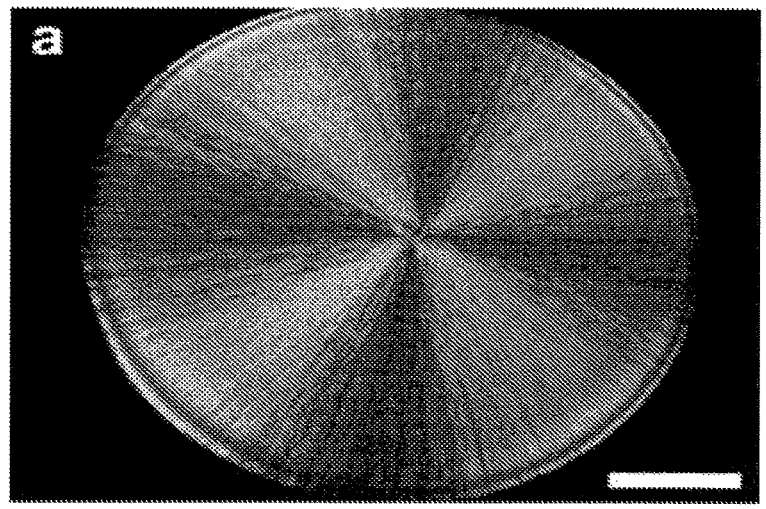
FIGS. 6A to 6F depict dendritic crystal growth within polymer solutions demonstrating many possible combinations of crystallizable molecules and polymers. The crystals were imaged by polarized light (FIGS. 6A to 6E) and phase contrast microscopy (FIG. 6F)
Figure 6B:
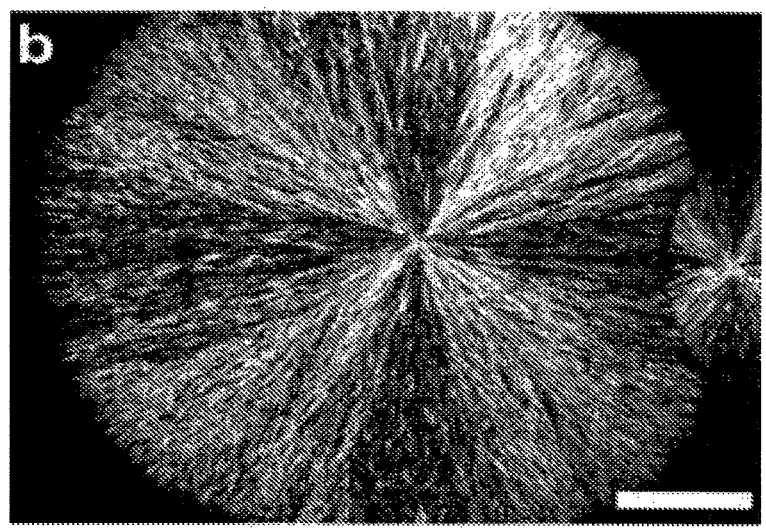
Figure 6C:
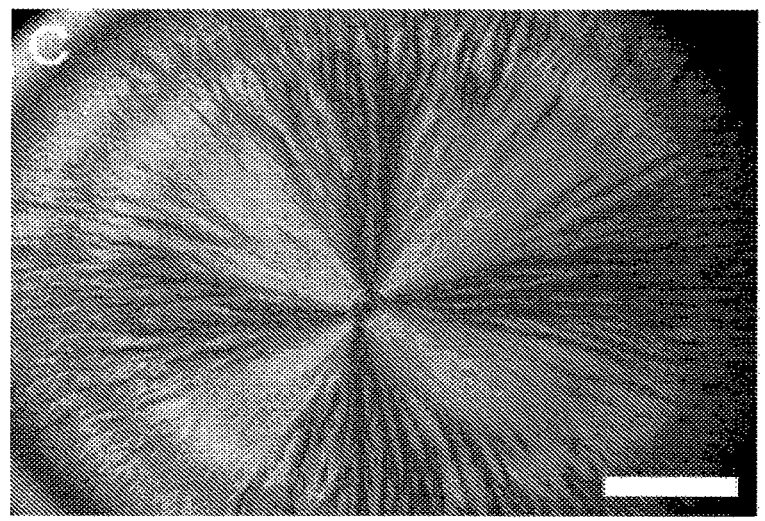
Figure 6D:
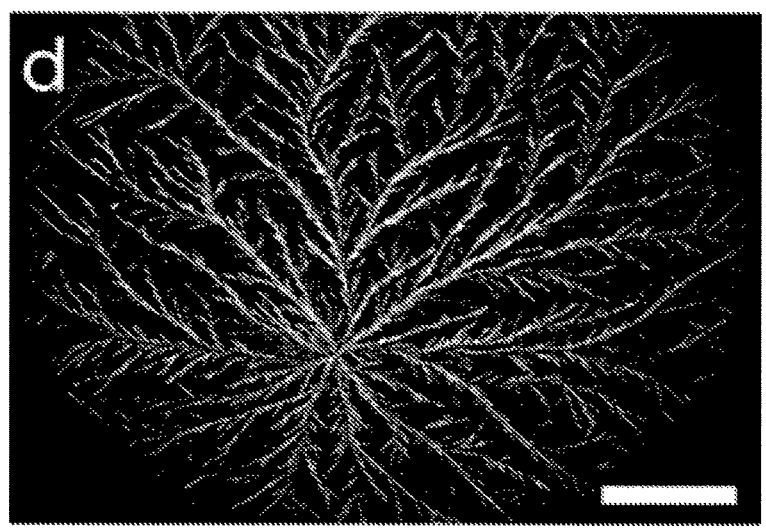
Figure 6E:
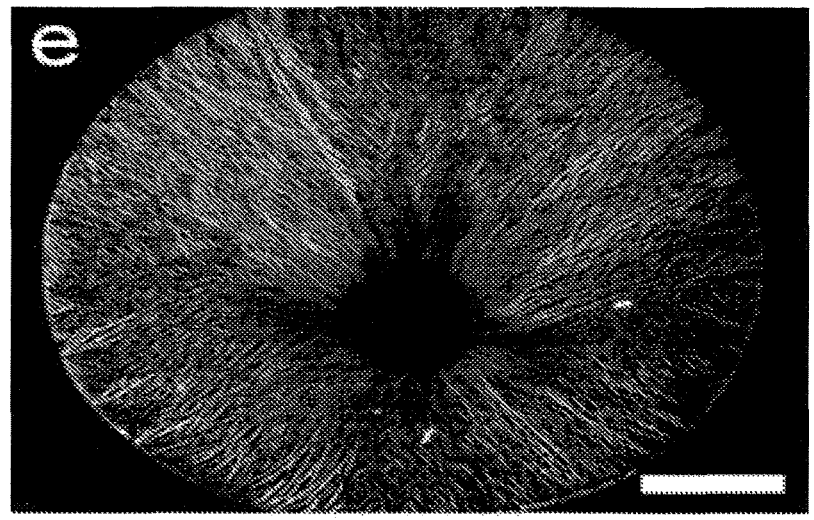
Figure 6F:
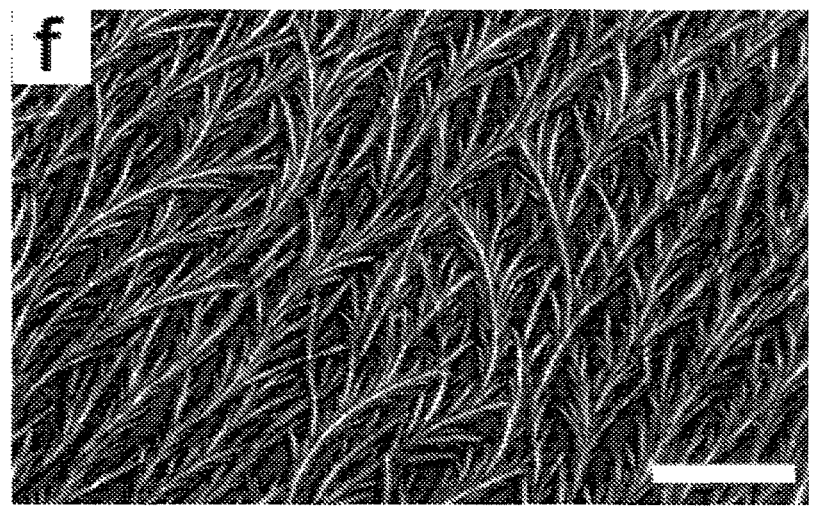

FIGS. 5A to 5F shows the process of urea-templating was scaled up from droplets to thick films. FIG. 5A is a photograph of scaled-up freestanding films of plain and urea-templated HA and alginate. FIGS. 5B to 5E are SEM images of crystal templated HA after crosslinking and rinsing. FIG. 5B is a top down view. HA hydrogel was sculpted into a "fibrous" morphology. In FIG. 5C, this portion of the film was curled back to expose the crevices in the hydrogel that had been created by urea crystals. FIG. 5D shows a cross-section of the hydrogel perpendicular to the pore orientation depicting that the pores are present throughout the thickness of the hydrogel. FIG. 5E is a parallel cross-section depicting the fibrillar morphology. FIG. 5F is a magnified view of FIG. 5E.

Crystal-templated films were opaque white and had a fibrillar morphology observable even by eye (FIG. 5A). In contrast, non-templated films of HA were transparent and featureless. Non-templated SA films were a light milky white and had a fine granular morphology when viewed under phase contrast microscopy. All templated and non-templated HA and SA films were durable, pliable and easy to handle in both dry and swollen conditions.

Scaled-up templated films were too thick for their features to be observed by optical microscopy; therefore, the morphology of these films was investigated by SEM. Dehydration of swollen hydrogel specimens can easily create artifacts in the hydrogel structure and particularly on the surface. To minimize such artifacts the SEM specimens were extensively soaked and rinsed with methanol rather than water to remove urea. Urea is highly soluble in methanol (.about.160 mg/mL) and the templated hydrogel swelled minimally. The urea crystals had been so tightly packed that the templated HA hydrogel had a fibrillar appearance. When observed from the topdown a repeating "arrowhead" fibrillar morphology of the film was clearly revealed (FIG. 5B). A curled portion of the film viewed at an angle revealed the interior crevices among the fibers that had contained the crystal template (FIG. 5C). Cross-sections of the film perpendicular and parallel to the fiber orientation are depicted in FIGS. 5D and 5E, respectively. These cross-sections demonstrate that the pore and fiber morphology was present throughout the thickness of the film and not confined to the surfaces; thus, confirming that the templates are three-dimensional.

The crystal-templating technique is different from existing technology because the crystals are grown within the hydrogel. That is, crystallization begins at a point of nucleation and then radiates outwards filling the entire three dimensional volume. This process of growth ensures that the resulting pores are interconnected and oriented. Importantly, the crystals are suspended within the viscous biopolymer solution permitting crystal growth in three dimensions. Scale-up can be achieved because crystallization occurs rapidly over large distances. Crystallization of urea within HA and SA hydrogels was both easily reproducible and highly robust with respect to the concentrations of urea and biopolymer. This robustness to concentration permitted the hydrogels to be scaled from droplets to large films. The formation of the crystal templates was, however, sensitive to ambient humidity which affected the rate of solvent evaporation and the final water content of the evaporated, equilibrated hydrogel films. This sensitivity was circumvented through the use of controlled humidity conditions. Although crystal-templating lacks precise control over the final pore morphology this can be alleviated through temporal and spatial control of the nucleation event through the use of seed nucleation.

In addition to hyaluronic acid and alginate poly(ethylene glycol) acrylate hydrogels are also patternable by urea crystallization. Exploration of other crystallites and crystal growth conditions will yield a range of template morphologies. For example, engineered potassium phosphate templates were determined that possess dendritic structures that are much larger and thicker than the urea templates. Crystal engineering is a set of techniques that tailors the supramolecular assembly of crystalline materials by manipulating crystal growth conditions. Important parameters are the concentrations and ratios of biopolymer and urea, solution viscosity, pH, and temperature. Additives such as surfactants and chiral molecules can selectively adhere to crystal faces and thereby control the branching, size and chirality of the resulting crystal structures [28]. Such techniques may be able to refine the crystal structures and to produce a wide selection of crystal templates.

The applications of crystal-templated hydrogels extend beyond tissue engineering because these hydrogels present a unique platform for the creation of composite materials. For example, infusion of the pores with cell adhesive proteins would be ideal for tissue engineering scaffolds. Polymerization reactions and biomineralization within the pores can yield novel composites in which one component is distributed throughout the other component in oriented dendritic micronsized pores.

Sodium hyaluronate from Streptococcus equi of molecular weight 1.6.times.10.sup.6 Da as indicated by supplier and low viscosity alginic acid from brown algae were obtained from Sigma-Aldrich (St. Louis, Mo.). Tetra-functional poly (ethylene glycol) acrylate (PEG4A, MW=10 kDa) was obtained from SunBio. Photoinitiator, Irgacure 2959, was obtained from Ciba Specialty Chemicals (Basel, Switzerland). Photopolymerizations were initiated by a longwave UV lamp filtered around 365 nm and with an intensity of 22 mW/cm2 (Blak-Ray B-100A, UVP, Upland, Calif.).

Photocrosslinkable HA was prepared by our standard procedure of derivatization of HA with glycidyl methacrylate to yield GMHA [25]. Urea-templated GMHA films were prepared as depicted in FIG. 1A. An aqueous solution was prepared of 10 mg/mL GMHA with 40 mg/mL urea and 0.5 mg/mL photoinitiator (Irgacure 2959) in distilled deionized water. Droplets of 2 .mu.L were dispensed onto a glass microscope slide. The solvent was partially evaporated overnight at ambient conditions or in sealed containers with .about.50% relative humidity maintained by saturated solutions of calcium nitrate. GMHA is very hygroscopic and retained residual moisture in equilibrium with the humid atmosphere.

Thus, evaporation yielded viscous hydrogel films that were super-saturated with urea. After drying, urea seed crystals were deposited onto the tips of a fine pair of tweezers by scraping the tweezers against solid urea. Then the tweezers were carefully touched to the center of each droplet to nucleate crystallization. Similarly, a razor-blade scraped against urea was used to nucleate straight lines. GMHA was crosslinked by 1 minute of exposure to UV. The hydrogels were rinsed in water to remove urea.

Templated alginate hydrogels were prepared as shown in FIG. 1B. Aqueous solutions of 10 mg/mL alginate with 40 mg/mL urea were dispensed onto microscope slides and air-dried. After crystallization the hydrogels were crosslinked by covering the droplet 200 mg/mL calcium chloride solution for one minute. Rinsing with water removed excess calcium chloride and urea.

Templated PEG4A hydrogels were prepared from aqueous solutions of 60 mg/mL PEG4A, 40 mg/mL urea and 0.5 mg/mL Irgacure 2959. Potassium phosphate templated GMHA was prepared from a solution of 20 mg/mL GMHA, 10 mg/mL potassium dihydrogen phosphate and 0.5 mg/mL Irgacure 2959. These droplets were incubated in humid chambers equilibrated with saturated sodium chloride solutions until crystal growth was complete.

Scale-up of Crystal Templated Hydrogels. Thick crystal-templated hydrogels were prepared under sterile conditions to prevent contamination during solvent evaporation. Aqueous solutions were prepared as described above, filter sterilized (0.22 .mu.m PVDF, Millipore), and dispensed into sterile, non-tissue culture treated 12-well plates. Each well was 2.2 cm in diameter and a volume of 2.6 mL of sterile solution was dispensed per well. The solvent was evaporated in a sterile horizontal flow hood in the dark for four days. During this time urea crystallization either nucleated spontaneously or was nucleated by the seed crystal technique. Once nucleated, crystallization is rapid and therefore spontaneously nucleated films had only one nucleation point. GMHA films were crosslinked by 1 minute of UV exposure, and rinsed extensively with exchanges of water over several days to remove urea. Alginate films were crosslinked by immersion in 200 mg/mL calcium chloride for twenty minutes and then rinsed extensively with water.

Plain GMHA films required an additional humidifying step after air-drying and before photocrosslinking This step was required because the photocrosslinking reaction was moisture sensitive. It is likely necessary for water to be retained within the film to permit diffusion of photoinitiator and movement of GMHA chains during photoexposure. Therefore, air-dried films were placed in a sealed container at .about.85% relative humidity which was achieved by equilibration with saturated potassium chloride solution. GMHA films were incubated under these conditions for four days and then photocrosslinked by 1 minute of exposure to UV.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. An apparatus comprising:
    a hydrogel film having first and second opposing ends;
    uncrosslinked hyaluronic acid included in the hydrogel; and crosslinked alginate included in the hydrogel;
wherein the alginate is crosslinked with calcium and the alginate is crosslinked around the uncrosslinked hyaluronic acid.

2. The apparatus of claim 1 comprising:
a continuous pore network, connecting the first and second ends, including first and second pore portions parallel to one another; and
a compressed fiber including a ridge compressed between the first and second pore portions.

3. The apparatus of claim 2, wherein the ridges include compressed hyaluronic acid.

4. The apparatus of claim 2, wherein the compressed fiber is included in a plurality of compressed fibers formed among alternating valleys and ridges.

5. The apparatus of claim 2, wherein the network includes a crystal.

6. The apparatus of claim 1, wherein the alginate is crosslinked with a calcium based salt.

7. The apparatus of claim 1, wherein the hydrogel further comprises at least one of a drug and a protein.

8. The apparatus of claim 2, wherein a geometrical pattern for the continuous pore network is determined in response to a ratio of the hyaluronic acid to the alginate.

9. The apparatus of claim 1, wherein the hyaluronic acid is not a derivative of hyaluronic acid.

10. The apparatus of claim 1 included in a kit comprising a calcium chelator.

11. The apparatus of claim 1, wherein the hydrogel film consists essentially of the uncrosslinked hyaluronic acid and the crosslinked alginate.

\* \* \* \* \*

UNITED STATES PATENT AND TRADEMARK OFFICE
CERTIFICATE OF CORRECTION

PATENT NO. : 8,728,499 B2
APPLICATION NO. : 13/909707
DATED : May 20, 2014
INVENTOR(S) : Scott Zawko et al.

Page 1 of 1

It is certified that error appears in the above-identified patent and that said Letters Patent is hereby corrected as shown below:

In the Specification

Column 1:
Line 16-22,

"STATEMENT OF FEDERALLY FUNDED RESEARCH

This invention was made with U.S. Government support under Contract No. BES-021744 and BES-0500969 awarded by the NSF. The government has certain rights in this invention."

should be

--STATEMENT OF FEDERALLY FUNDED RESEARCH

This invention was made with government support under Grant no. BES0201744 and BES0500969 awarded by the National Science Foundation. The government has certain rights in the invention.--

Signed and Sealed this
Twenty-sixth Day of May, 2015

Michelle K. Lee
*Director of the United States Patent and Trademark Office*